US00PP33835P2

(12) United States Plant Patent
Denardi et al.

(10) Patent No.: US PP33,835 P2
(45) Date of Patent: Jan. 11, 2022

(54) APPLE TREE NAMED 'ISADORA'

(50) Latin Name: ***Malus domestica* Borkh.**
Varietal Denomination: Isadora

(71) Applicant: Empresa de Pesquisa Agropecuária e Extensão Rural de Santa Catarina S.A. (Epagri), Santa Catarina (BR)

(72) Inventors: Frederico Denardi, Santa Catarina (BR); Marcus Vinicius Kvitschal, Santa Catarina (BR); Maraisa Crestani Hawerroth, Rio Grande do Sul (BR)

(73) Assignee: Empresa de Pesquisa Agropecuaria e Estensao Rural de Santa Catarina S.A., Santa Catarina (BR)

( * ) Notice: Subject to any disclaimer, the term of this patent is extended or adjusted under 35 U.S.C. 154(b) by 0 days.

(21) Appl. No.: 17/300,212

(22) Filed: Apr. 14, 2021

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
CPC ... A01H 5/08; A01H 5/00; A01H 5/02; A01H 6/74; A01H 6/7418
See application file for complete search history.

(56) References Cited

PUBLICATIONS

Upov International Union for the Protection of New Varieties of Plants Apple Guidelines for the Conduct of Tests for Distinctness, Uniformity and Stability TG/14/9, 2005, (retrieved from the Internet at https://www.upov.int/edocs/tgdocs/en/tg014.pdf, pp. 1 and 28. (Year: 2005).*

* cited by examiner

*Primary Examiner* — June Hwu
(74) *Attorney, Agent, or Firm* — Michelle Bos Legal LLC

(57) ABSTRACT

A new apple tree named 'Isadora' apple tree, distinguished by its suitability for growing regions with low chilling hours; immunity to Glomerella leaf spot (*Colletotrichum* spp.); and relatively late harvest window as compared to varieties grown in the same low-chill regions. 'Isadora' is further notable for its fruit, which has very good flavor and sweetness and is firm and very crunchy. The fruit of 'Isadora' does well in long-term storage.

8 Drawing Sheets

Latin name: *Malus domestica* Borkh.
Variety denomination: 'Isadora'.

BACKGROUND OF THE VARIETY:

'Isadora' is a new and distinct variety of apple tree (*Malus domestica* Borkh) obtained from a controlled cross of 'Cripps Pink' (female parent, U.S. Plant Pat. No. 7,880) x 'Imperatriz' (male parent, not patented) carried out at Caçador, Santa Catarina, Brazil in 2001. Seeds obtained from the cross were planted at Caçador, and 'Isadora' was selected from the resulting seedlings for propagation and further observation under breeder's reference 'M 10/09'. 'Isadora' was first asexually propagated by bench grafting onto M.9 rootstock (not patented) at Caçador in 2004, and has since been observed to remain true to type through successive asexually propagated generations.

BRIEF DESCRIPTION OF THE VARIETY

The 'Isadora' apple tree is distinguished by its suitability for growing regions with low chilling hours; immunity to Glomerella leaf spot (*Colletotrichum* spp.); and relatively late harvest window as compared to 'Gala' and 'Fuji' varieties grown in the same low-chill regions. 'Isadora' is further notable for its fruit, which has very good flavor and sweetness and is firm and very crunchy. The fruit of 'Isadora' does well in long-term storage.

Comparisons of 'Isadora' to its parents and to similar variety 'Alpigala' (U.S. Plant Pat. No. 30,061) are shown in Tables 1, 2 and 3 below.

TABLE 1

Comparison of 'Isadora' to Female Parent 'Cripps Pink'

| Characteristic | 'Isadora' | 'Cripps Pink' |
|---|---|---|
| Pattern of overcolor | Weakly defined flush with strongly defined stripes | Solid flush |
| Amount of overcolor | About 80% | 50% to 60% |
| Juiciness | More juicy than 'Cripps Pink' | Less juicy than 'Isadora' |
| Russeting of skin | Very little on cheeks; moderate around stalk cavity | None |
| Harvest timing | One week earlier than 'Cripps Pink' | One week later than 'Isadora' |

TABLE 2

Comparison of 'Isadora' to Male Parent 'Imperatriz'

| Characteristic | 'Isadora' | 'Imperatriz' |
|---|---|---|
| Fruit size | Smaller than 'Imperatriz' | Larger than 'Isadora' |
| Fruit skin | Thicker | Thinner |
| Tree vigor | Moderate | Vigorous |

TABLE 2-continued

| Comparison of 'Isadora' to Male Parent 'Imperatriz' | | |
|---|---|---|
| Characteristic | 'Isadora' | 'Imperatriz' |
| Tree habit | Spreading | Upright |
| Fruit storageability | 6 months | 3 months |

TABLE 3

| Comparison of 'Isadora' to Similar Variety 'Alpigala' | | |
|---|---|---|
| Characteristic | 'Isadora' | 'Alpigala' |
| Fruit overcolor | Red 45A | Purple N77A |
| Firmness of fruit flesh | 10.6 kg/cm$^2$ | 7.1 kg/cm$^2$ |
| Harvest timing | Later (October) | Earlier (early September) |
| Tree bark color | Grey-brown 199C | Brown 200C |
| Date of full bloom (2018) | Apr. 19 | Apr. 23 |

BRIEF DESCRIPTION OF THE PHOTOGRAPHS

The accompanying photographs were taken at Seiches sur le Loir, France of trees planted in 2016. Flower photos were taken in 2018, fruit photos in 2019, and leaves and additional fruit photos in 2020.

DETAILED BOTANICAL DESCRIPTION OF THE VARIETY

Figure 1:
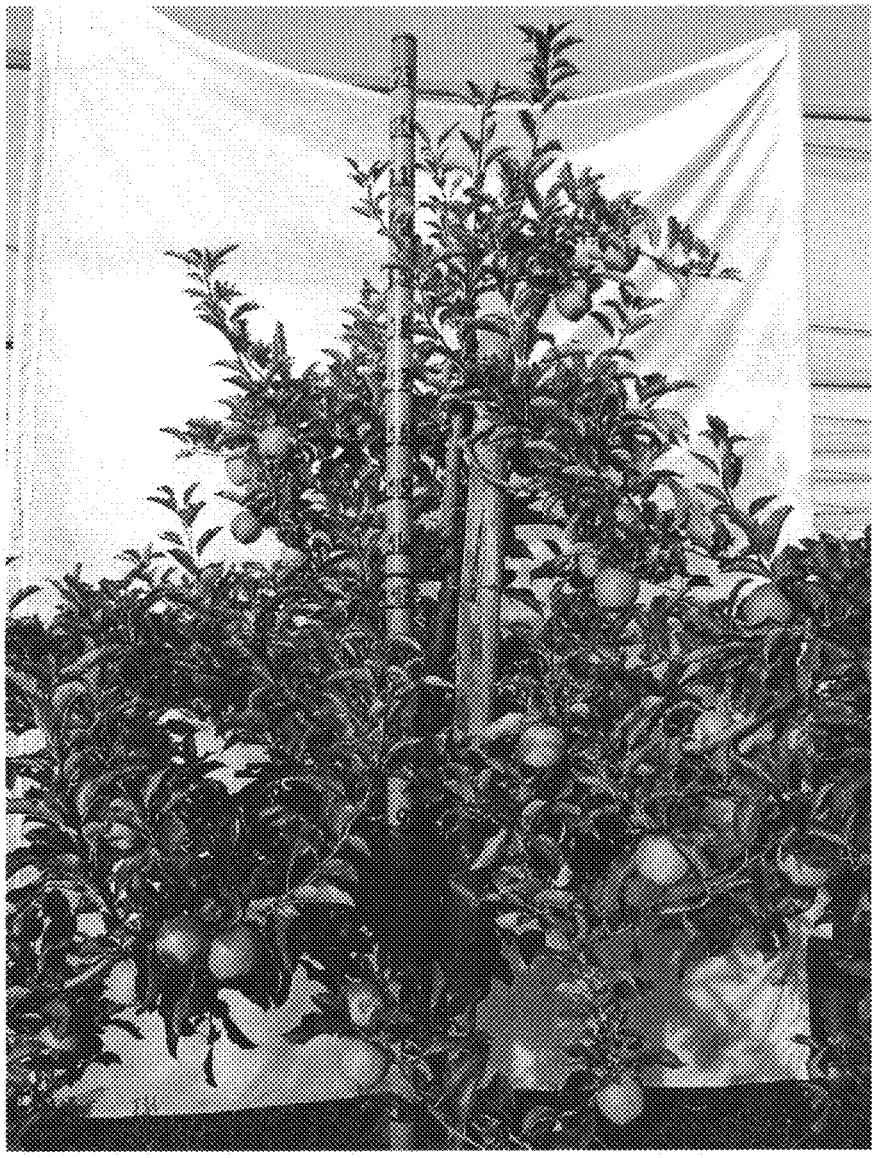
FIG. 1 is a photograph of an 'Isadora' apple tree with leaves and fruit.
Figure 2:
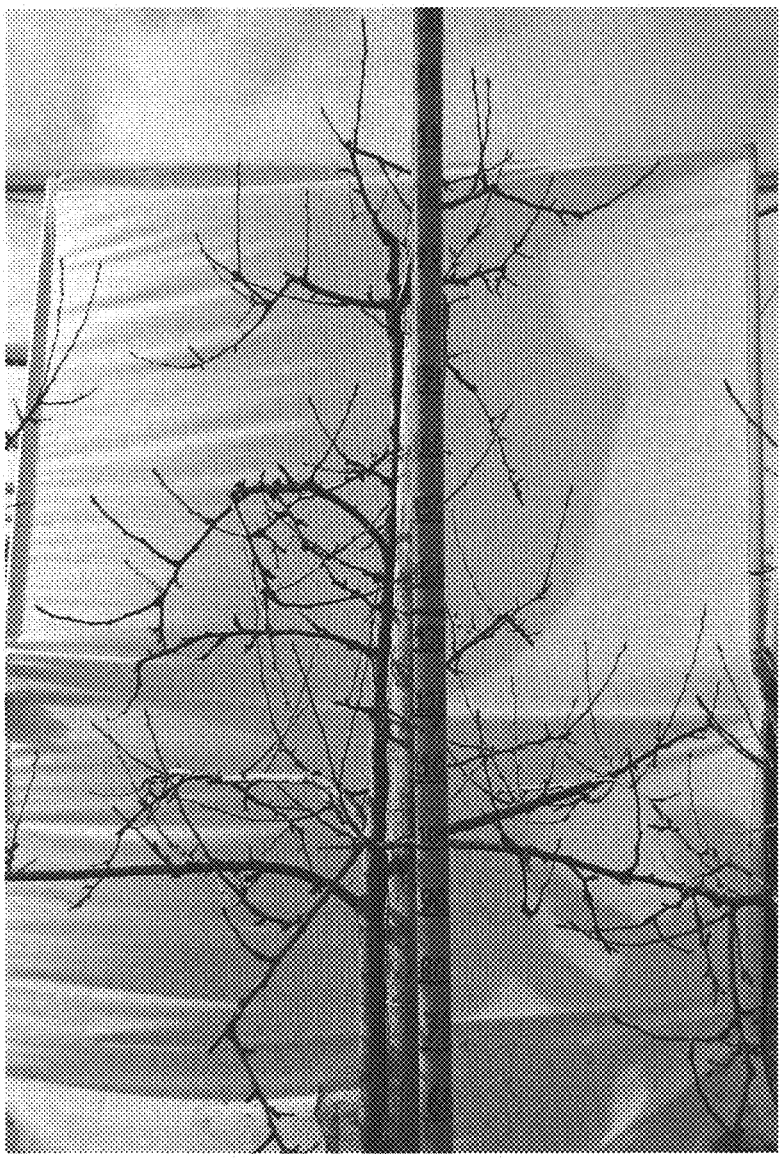
FIG. 2 is a photograph of a bare 'Isadora' apple tree.
Figure 3:
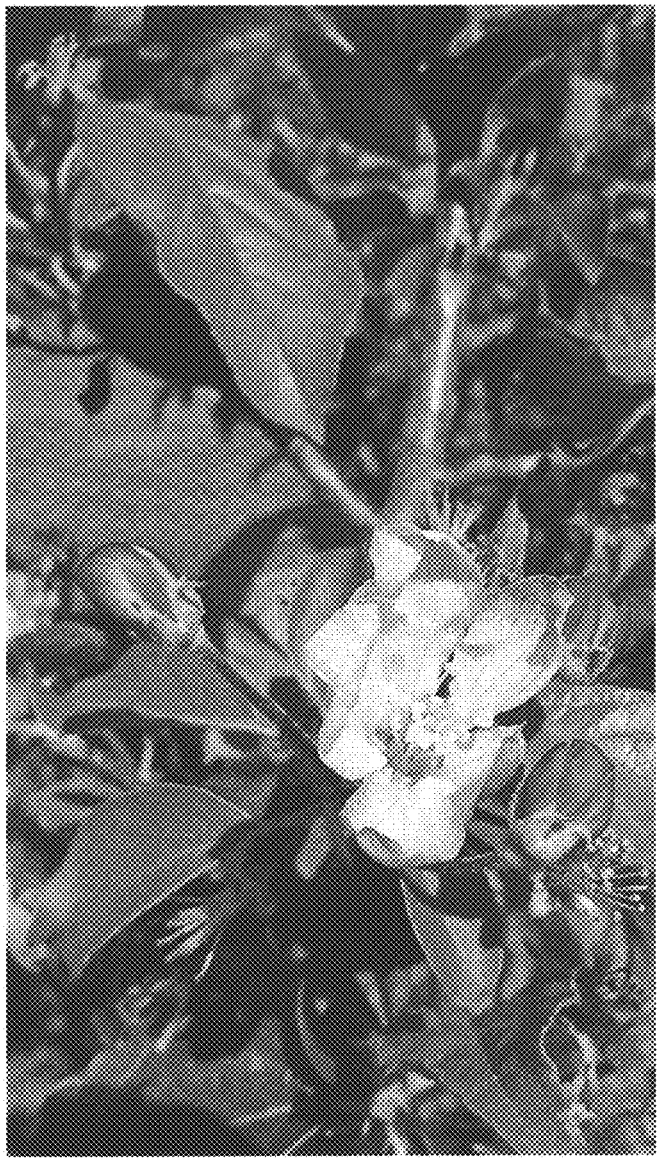
FIG. 3 is a photograph of a flower of an 'Isadora' apple tree.
Figure 4:
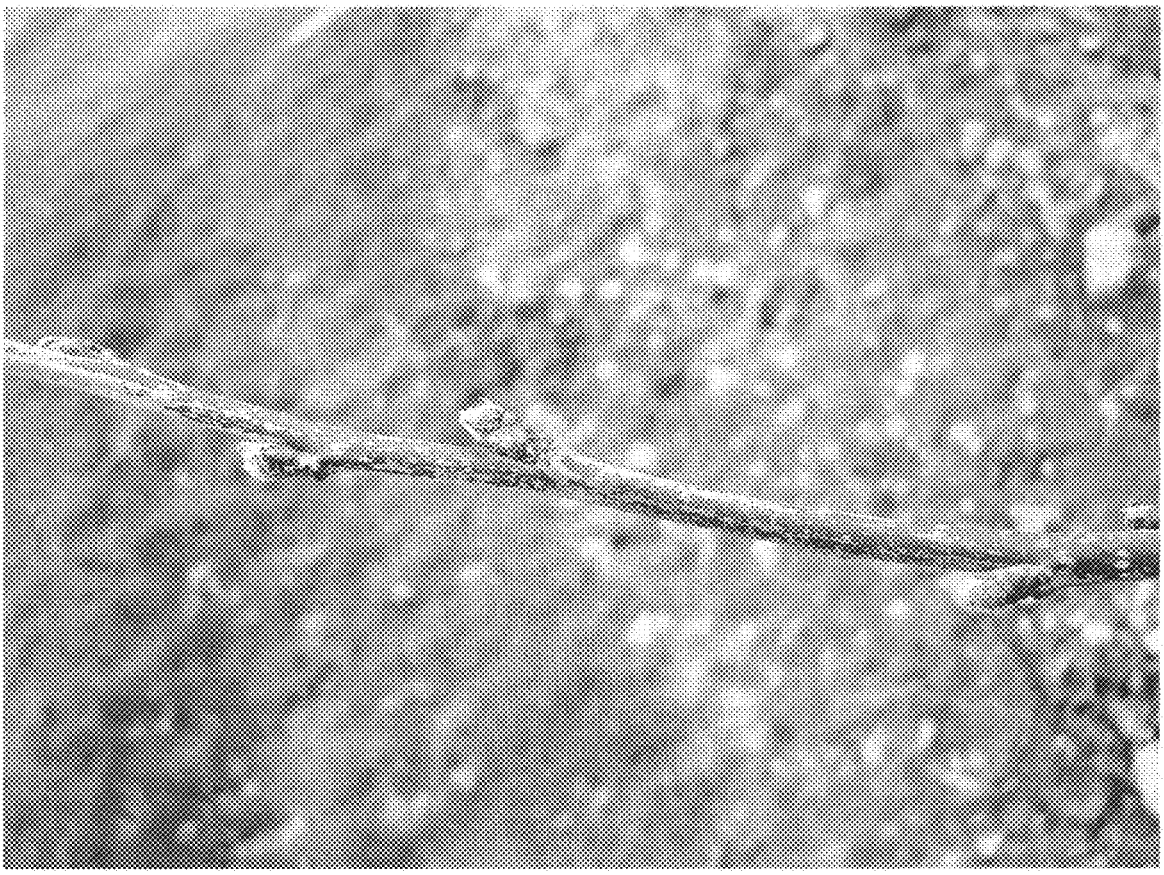
FIG. 4 is a photograph of a one-year-old shoot of an 'Isadora' apple tree.
Figure 5:
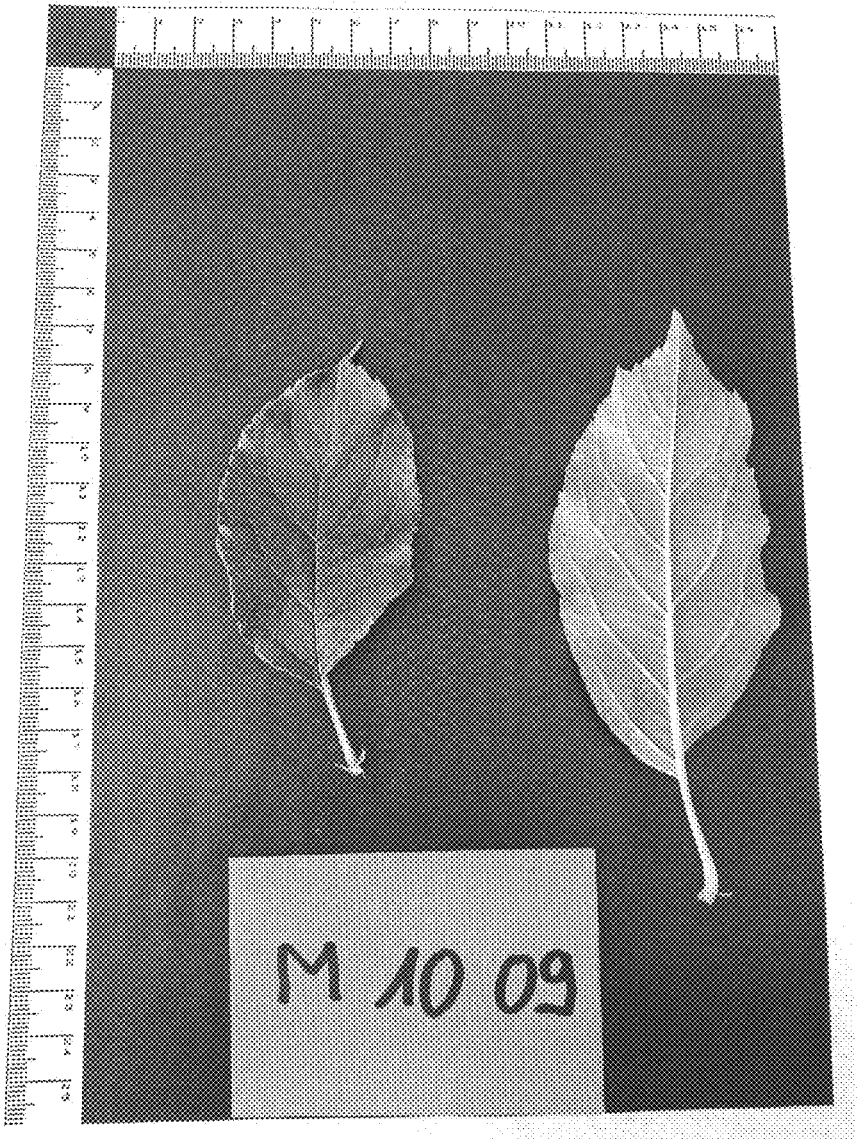
FIG. 5 is a photograph of leaves of an 'Isadora' apple tree.
Figure 6:
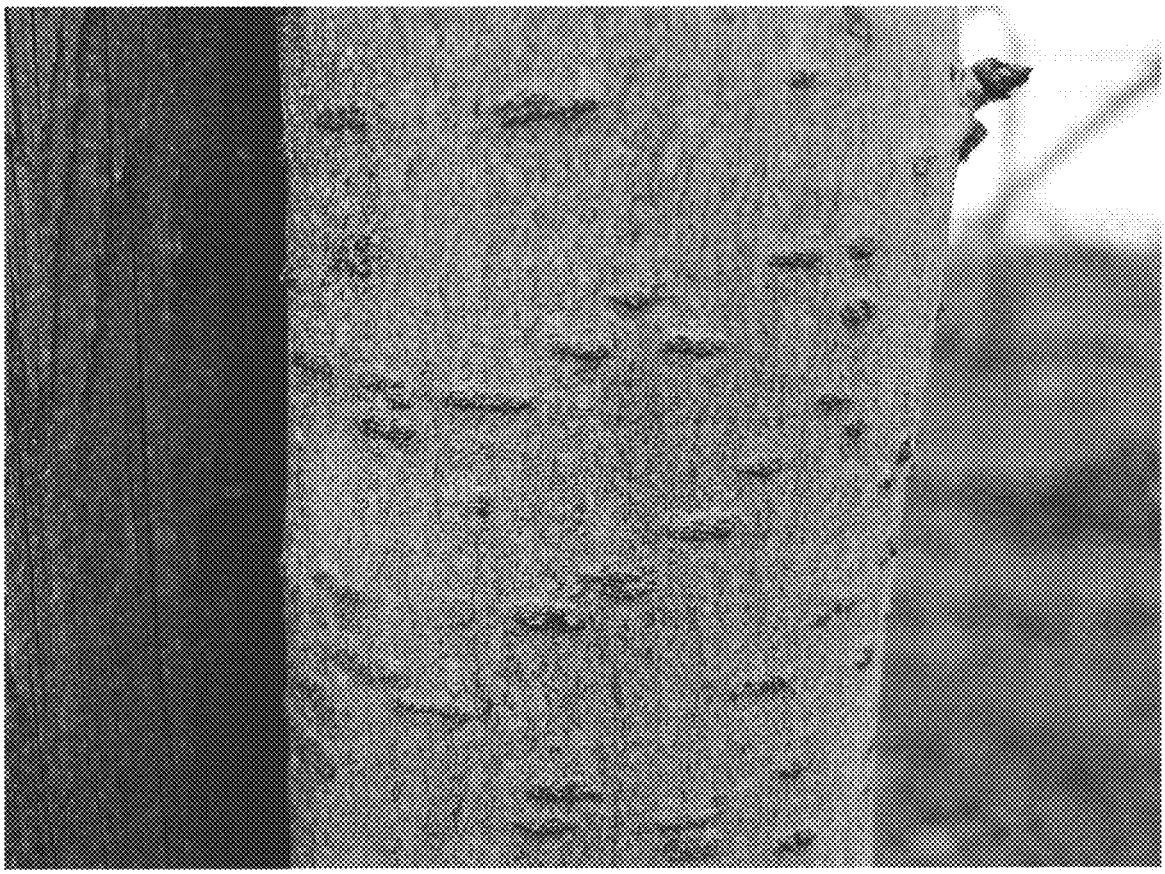
FIG. 6 is a photograph of the trunk of an 'Isadora' apple tree.
Figure 7:
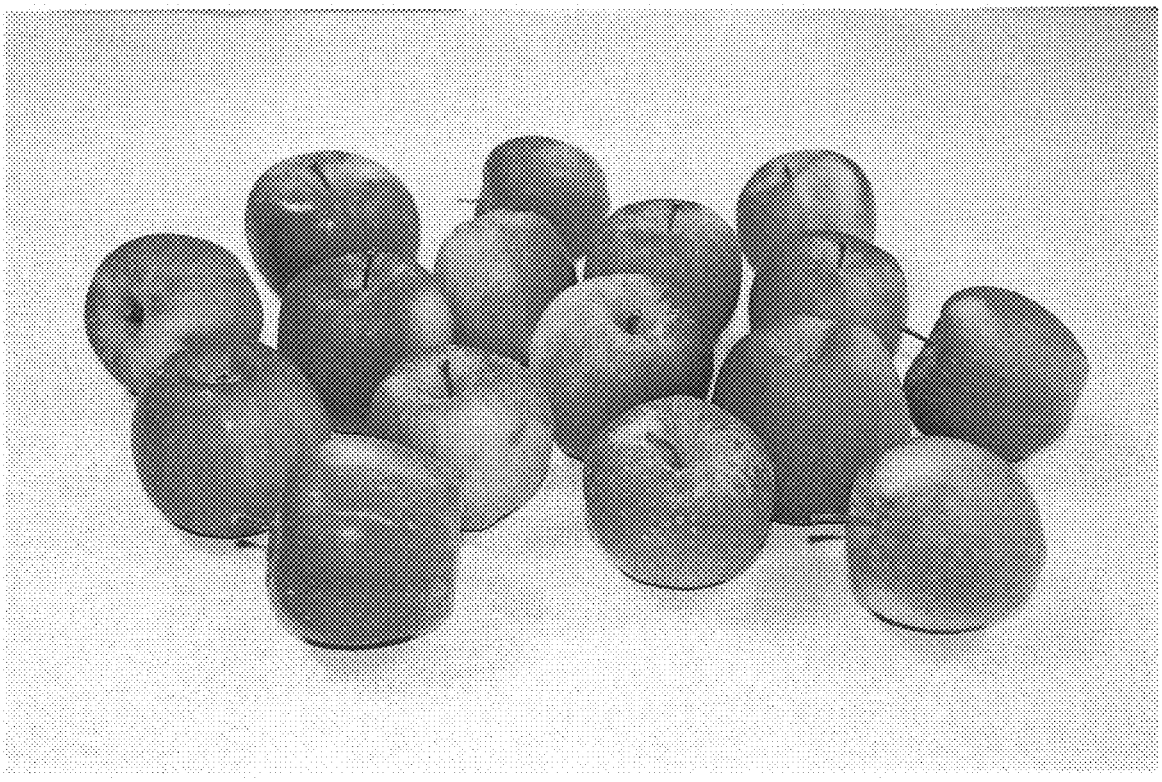
FIG. 7 is a photograph of whole fruit from an 'Isadora' apple tree.
Figure 8:
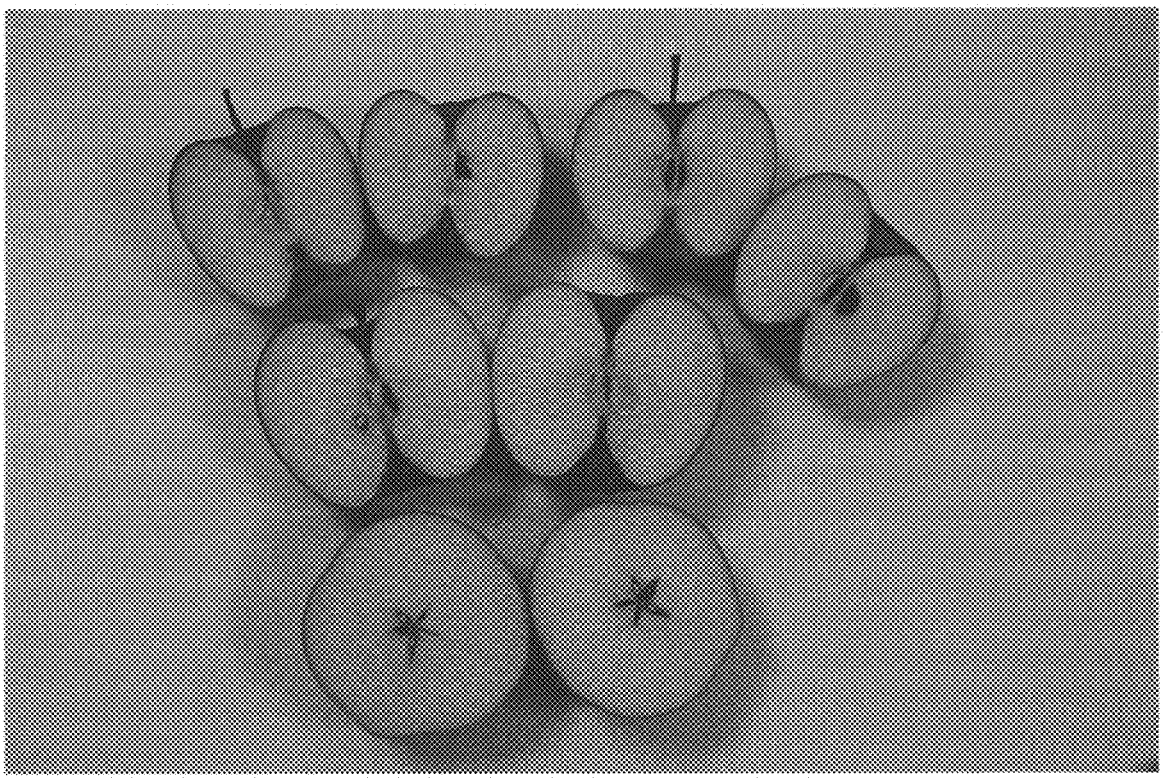
FIG. 8 is a photograph of sectioned fruit from an 'Isadora' apple tree.

The following detailed botanical description were obtained at Seiches sur le Loir, France during 2019 unless otherwise noted, of trees planted in 2016 and grown on Pajam®2 'Cepiland' (U.S. Plant Pat. No. 7,715) rootstock. All colors are described according to The R.H.S. Colour Chart (Royal Horticultural Society, 6$^{th}$ ed. 2019 reprint). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium.
*Type*.—Ramified.
*Habit*.—Spreading.
*Bearing*.—On shoots.
*Spread of mature tree*.—1.5 meters (after pruning).
*Height*.—2.0 m (after pruning).
*Trunk diameter* (*at* 30 *cm above the graft*).—48 mm.
*Bark texture*.—Slightly rough.
*Bark color*.—Grey-brown 199C tinged with yellow-orange 22A.
*Lenticel length*.—5 mm.
*Lenticel width*.—2 mm.
*Lenticel height*.—1 mm.
*Lenticel shape*.—Oblong.
*Lenticel color*.—Grey-brown 199C.
*Lenticel density*.—2 per cm$^2$.

Branch (fruiting branches located at around 1 m above the graft union):

*Length*.—90 cm.
*Diameter*.—17.8 mm.
*Crotch angle*.—60°.
*Bark color*.—Grey-brown 199C.
*Lenticel length*.—2 mm.
*Lenticel width*.—1 mm.
*Lenticel height*.—0.5 mm.
*Lenticel shape*.—Oblong.
*Lenticel color*.—Yellow-white 158A.
*Lenticel density*.—6 per cm$^2$.

One year old shoot:

*Length*.—28 cm.
*Diameter*.—5 mm.
*Color*.—Greyed-orange 165A.
*Pubescence*.—Weak.
*Internode length*.—4 cm.
*Lenticel length*.—1 mm.
*Lenticel width*.—1 mm.
*Lenticel height*.—0.5 mm.
*Lenticel shape*.—Round.
*Lenticel color*.—Yellow-white 158A.
*Lenticel density*.—Few.

Flower buds (at balloon stage):

*Quantity per spur*.—5 to 7.
*Bud shape*.—Conical to round.
*Apex shape*.—Round.
*Length*.—11 mm.
*Diameter*.—11 mm.
*Color*.—Red-purple 58A.

Flowers:

*Diameter of fully open flower*.—37 mm.
*Flower depth/height*.—12 mm.
*Relative position of petal margin* (*overlapping, touching, or free*).—Overlapping.
*Number per cluster*.—5 to 7.
*Fragrance*.—Strong.
*Date of first bloom*.—April 16$^{th}$ (2018, Loire Valley, France) 2 days before 'Golden Delicious' (not patented).
*Date of full bloom*.—April 19$^{th}$ (2018, Loire Valley, France) 4 days before 'Golden Delicious'.
*Pollination requirement*.—Pollenizer required; 'Granny Smith', 'Idared', 'Golden Gem' (none patented).

Petals:

*Number per flower*.—5.
*Petal shape*.—Elliptical.
*Length*.—21 mm.
*Width*.—14 mm.
*Apex shape*.—Rounded.
*Base shape*.—Acuminate.
*Margin*.—Smooth.

*Color of upper surface*.—White N155D with red-purple N74C.
*Color of lower surface*.—White N155D with red-purple 70B.

Pistils:
*Quantity*.—5.
*Length*.—12.5 mm.
*Color*.—Yellow-green 145B with yellow-green 146C.

Stigma:
*Length*.—1 mm.
*Color*.—Yellow-green 145B.
*Position relative to anthers*.—Same level.

Style:
*Length*.—9.4 mm.
*Color*.—Yellow-green 145B.

Ovary:
*Length*.—2.1 mm.
*Width*.—1.4 mm.
*Color*.—Yellow-green 146C.

Anthers:
*Quantity*.—19 to 20.
*Length*.—1.5 mm.
*Width*.—1.3 mm.
*Color of anther*.—Yellow 8C.
*Presence of pollen*.—Present in moderate quantities.
*Color of pollen*.—Yellow 8C.

Pedicel:
*Length*.—24 mm.
*Diameter*.—1 mm.
*Color*.—Greyed-purple 183A.

Sepals:
*Quantity*.—5.
*Color of upper surface*.—Yellow-green 145B.
*Color of lower surface*.—Yellow-green 145B.
*Length*.—7 mm.
*Width*.—3 mm.
*Sepal shape*.—Acuminate.
*Apex shape*.—Pointed.
*Margin*.—Smooth, pubescent.

Leaves:
*Shape*.—Ovate
*Length*.—99 mm.
*Width*.—47 mm.
*Blade margin*.—Serrate.
*Apex*.—Acute.
*Base shape*.—Wedge-shaped, asymmetric.
*Profile in cross section*.—Flat.
*Leaf color—upper surface*.—Green 137A, primary vein yellow-green 149D.
*Leaf color—lower surface*.—Greyed-green 194A.
*Attitude in relation to shoot*.—Upward.

Petiole:
*Length*.—27 mm.
*Diameter*.—2 mm.
*Color*.—Yellow-green 149D with greyed-purple 185B near base.

Fruit:
*Quantity per cluster*.—5.
*Diameter*.—74 mm.
*Height*.—67 mm.
*Ratio of height to width*.—0.9.
*Weight*.—169 g.
*General shape in profile*.—Globose.
*Position of maximum diameter*.—At equator.
*Ribbing*.—Moderate.
*Crowning at calyx end*.—Strong.
*Bloom of skin*.—Absent or weak.
*Greasiness of skin*.—Weak.
*Background color of skin*.—Yellow 4A at harvest; yellow 7D after storage.
*Over color of skin*.—Red 47A at harvest; red 45A after storage.
*Amount of over color*.—80%.
*Intensity of over color*.—Medium to dark.
*Pattern of over color*.—Weakly defined flush with strongly defined stripes.
*Width of stripes*.—Medium.
*Lenticel density*.—Medium.
*Lenticel size*.—Medium.
*Amount of russet around stalk cavity*.—Medium.
*Amount of russet on cheeks*.—Very small.
*Area of russet around eye basin*.—Absent.
*Length of stalk*.—27 mm.
*Diameter of stalk*.—2 mm.
*Stalk color*.—Greyed-orange 165A.
*Depth of stalk cavity*.—17 mm.
*Width of stalk cavity*.—36 mm.
*Depth of eye basin*.—9 mm.
*Width of eye basin*.—31 mm.
*Diameter of eye*.—7 mm.
*Length of sepal*.—6 mm.
*Firmness of flesh*.—10.6 kg/cm$^2$.
*Flesh texture*.—Medium, somewhat granular.
*Number of locules*.—5.
*Locule length*.—14 mm.
*Locule width*.—10 mm.
*Aperture of locules*.—Moderately open.
*Aroma, flavor*.—Sweet, subtle flavor.
*Juiciness*.—Very juicy.
*Brix*.—14.9° Brix.
*Flesh color*.—Yellow 4D.

Seeds:
*Quantity per fruit*.—Average 9.8.
*Length*.—9 mm.
*Width*.—5 mm.
*Shape*.—Elongated oval.
*Color*.—Greyed-orange N167A.

Harvest:
*Harvest date*.—October 23 (2019); between 'Fuji' and 'Cripps Pink'.
*Number of picks*.—2.
*Harvest yield*.—22 kg per tree (2020 harvest from trees planted in 2016).

Disease resistance/susceptibility: Resistance to Glomerella leaf spot (*Colletotrichum* spp.).
Eating quality: Very good.
Shipping quality: Good.
Storageability: Long, up to 6 months.
Market use: Fresh consumption.

The invention claimed is:

1. A new and distinct apple tree named 'Isadora' substantially as described and illustrated herein.

* * * * *